United States Patent
Rufin

(10) Patent No.: US 7,152,487 B2
(45) Date of Patent: Dec. 26, 2006

(54) NONDESTRUCTIVE VERIFICATION OF MINIMUM TENSILE ELONGATION OF MANUFACTURED PARTS

(75) Inventor: Antonio C. Rufin, Seattle, WA (US)

(73) Assignee: The Boeing Company, Chicago, IL (US)

( * ) Notice: Subject to any disclaimer, the term of this patent is extended or adjusted under 35 U.S.C. 154(b) by 118 days.

(21) Appl. No.: 10/962,045

(22) Filed: Oct. 7, 2004

(65) Prior Publication Data

US 2006/0075827 A1   Apr. 13, 2006

(51) Int. Cl.
*G01N 3/08* (2006.01)

(52) U.S. Cl. ....................................... 73/826
(58) Field of Classification Search ............. 73/826, 73/837, 863.32, 864.14
See application file for complete search history.

(56) References Cited

U.S. PATENT DOCUMENTS 5,083,465 A * 1/1992 Myers .................... 73/826
6,973,845 B1 * 12/2005 Bell ...................... 73/864.14

* cited by examiner

*Primary Examiner*—Jewel Thompson
(74) *Attorney, Agent, or Firm*—Don C. Lawrence; MacPherson Kwok Chen & Heid LLP

(57) ABSTRACT

The minimum tensile elongation specification of a manufactured part, such as metal castings, forgings and premium mill products, is verified in-situ using a simple, inexpensive, nondestructive apparatus and method in which a through-hole is formed in the part to be tested. A disposable mandrel having a diameter adapted to expand the hole to the minimum elongation required in the part's specification is pressed into the hole. The presence of radial cracks in the part adjacent to the hole after the mandrel has been pressed in indicates that the part does not meet the specification, and the absence of such cracks indicates that it does. Since the test is performed on the part itself, the cost of the manufacture and testing of tensile test coupons is eliminated, and different areas of the part may be sampled easily, thereby enabling a closer, more thorough evaluation of part's material bulk properties.

20 Claims, 3 Drawing Sheets

NONDESTRUCTIVE VERIFICATION OF MINIMUM TENSILE ELONGATION OF MANUFACTURED PARTS

TECHNICAL FIELD

This invention relates to the nondestructive testing of manufactured parts in general, and in particular, to apparatus and methods for the nondestructive, in-situ verification of the minimum tensile elongation specification of metal castings, forgings, and premium mill products such as plate, bar and extrusion, and molded parts and the like.

BACKGROUND

Specifications for metal castings, forgings and premium mill products such as plate, bar and extrusion, frequently include tensile elongation minima among their lot acceptance requirements. Elongations are measured using tensile test specimens, e.g., "coupons," made from specially cast bars ("prolongs"), or material that is excised from the manufactured parts themselves, which are stretched in specialized tensile testing machines. In addition to the cost of the materials consumed in these tests, there are also significant costs associated with the machining and testing of the specimens. Furthermore, the specimens may not adequately represent the true bulk material properties of the parts being evaluated, which can lead to erroneous test results.

A long-felt but as yet unsatisfied need therefore exists in the manufacturing industry for reliable, low-cost, apparatus and methods for the nondestructive verification of the minimum tensile elongation specification of a manufactured part that can be effected on the part itself, thereby eliminating the need for expensive tensile test coupons and equipment, and any question whether such coupons accurately represent the true bulk material properties of the manufactured part.

BRIEF SUMMARY

In accordance with an embodiment of the present invention, simple yet reliable, low-cost apparatus and methods are provided for the nondestructive, in-situ verification of the minimum tensile elongation specification of a manufactured part that eliminate the need for tensile coupons, and any question whether such coupons accurately represent the actual bulk properties of the manufactured part. Since the non-destructive elongation measurements are made within the parts themselves, material pedigree is no longer an issue. Advantageously, the novel method also applies stresses to a greater amount of the material of the part, and can easily sample different areas of the part, thereby enabling a closer, more thorough evaluation of the part's material bulk properties.

In an exemplary embodiment thereof, the apparatus of the invention includes a simple, disposable, elongated mandrel having opposite first and second ends. A small, first cylindrical portion is disposed adjacent to the first end of the mandrel to define a pilot end portion thereof. A larger second cylindrical portion is disposed adjacent to the second end of the mandrel to define a hole-expanding end portion thereof. A first axial taper extends between the first and second portions. A second axial taper may extend between the first end of the mandrel and the first portion thereof, and a third axial taper may extend between the second portion and the second end thereof. Advantageously, the second, or pushing end of the mandrel may be rounded to form a spherical bearing surface. In one possible embodiment, the mandrel is made of a hard, structural ceramic, such as silicon nitride or a tool steel. An exterior surface of the mandrel may be coated with a hard, low-friction coating, e.g., a baked-on, thin-film lubricant.

In accordance with an exemplary embodiment of the method of the invention, the mandrel functions in cooperation with a pre-lubricated through-hole having a specific diameter H that is formed in the manufactured part, e.g., a casting or a forging, having a minimum tensile elongation specification "e," expressed as a percentage, which is to be tested. The second, hole-expanding portion of the mandrel has a diameter D that is related to the tensile elongation specification e and the diameter H of the test through-hole by the relationship, $$D = \left(\frac{e}{100} + 1\right) \cdot H,$$

and is thereby adapted to expand the diameter of the hole to the minimum elongation e required in the specification when the mandrel is pressed into the hole. Thus, the pilot end of the mandrel is inserted into a first, or front, end of the test hole, and the mandrel is then pressed fully into the hole, e.g., with a benchtop press ram, until the second end of the mandrel is about flush, or coplanar with, the first end of the hole. After the mandrel has been pressed into the hole, the region of the part adjacent to the first end of the hole is inspected, e.g., visually, or by fluorescent dye penetrant, for radial cracks. The presence of radial cracks in the part adjacent to the hole indicates that the manufactured part does not meet the specification, and the absence of such cracks indicates that it does.

For parts that are relatively thick, the mandrel may be pressed further into the hole, until the second portion of the mandrel is disposed at a second, or back end of the hole, and the back of the part adjacent to the second end of the hole may also be inspected for radial cracks. For parts that are relatively thin, the front and back surface inspections may be performed concurrently, without further insertion of the mandrel into the test hole. When the test is complete, the mandrel is expelled from the test hole and discarded.

A better understanding of the above and many other features and advantages of the invention may be obtained from a consideration of the detailed description thereof below, particularly if such consideration is made conjointly with the appended drawings.

DETAILED DESCRIPTION

In accordance with an exemplary embodiment of the present invention, an inexpensive, disposable mandrel 10 and a few simple bench tool accessories are used in conjunction with a method to radially expand a test hole formed in a casting, forging, or other manufactured part by a prescribed amount to effect a circumferential strain at the edge of the hole matching minimum required elongation, or target strain, of the part. After the test hole has been radially expanded, the area in the vicinity of the test hole is inspected for radial cracks, which indicate that the part does not meet the elongation minima requirements. The apparatus and method can be used either to complement or completely replace existing standard tensile tests.

Figure 1:
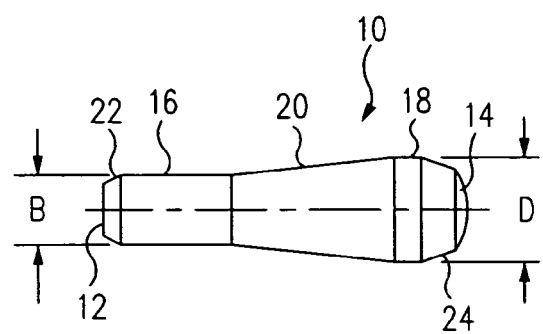
FIG. 1 is a side elevation view of an exemplary embodiment of an expansion mandrel in accordance with the present invention.

As illustrated in FIG. 1, the apparatus of the invention comprises an elongated, tapered mandrel 10 that is used to radially expand a pre-lubricated test hole that has been formed in the part to be tested. The mandrel has opposite, respective first and second ends 12 and 14. A small, first cylindrical portion 16 is disposed adjacent to the first end of the mandrel, and defines a "pilot" end portion thereof. A larger second cylindrical portion 18 is disposed adjacent to the second end of the mandrel, and defines a hole-expanding end portion thereof. A first axial taper 20 extends between the first and second portions. Advantageously, a second axial taper 22 may extend between the first end of the mandrel and the first portion thereof, and a third axial taper 24 may extend between the second portion and the second end thereof. Optionally, the second end 14 of the mandrel may be rounded to form a spherical-segment bearing surface thereat.

Figure 2:
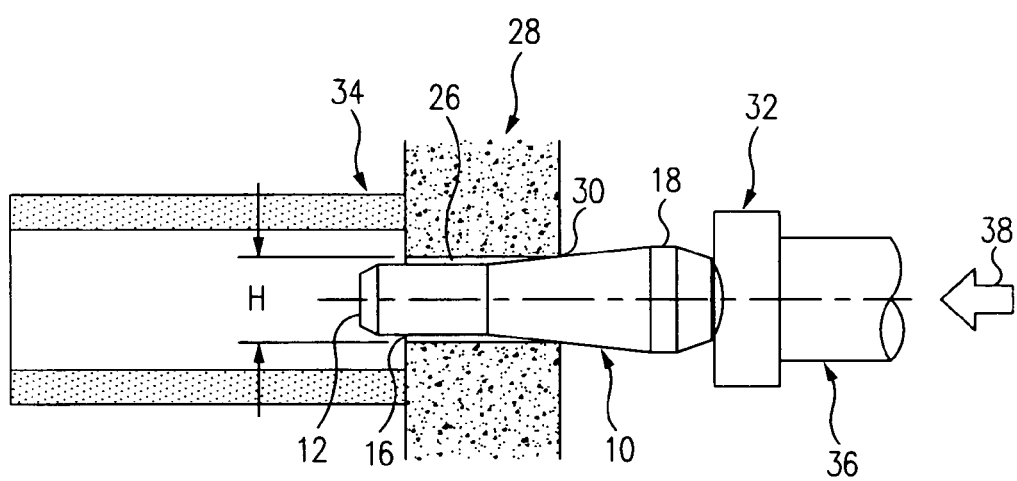
FIG. 2 is a partial cross-sectional elevation view of the exemplary mandrel being pressed into a first end of a test hole of a manufactured part.

In accordance with one embodiment of the method of this invention, a test hole 26, as illustrated in FIG. 2, is located in a region of the part 28 where a tensile strain (i.e., elongation) measurement is desired. Radial cold expansion of a hole can be accomplished using a variety of techniques, the most common of which are (a) pull-type, sleeve-assisted expansion, (b) pull-type split-mandrel expansion, (c) pull-type solid-mandrel expansion, and (d) push-mandrel expansion. A problem with cold expansion of a hole using a standard "sleeve" process is that the hole, sleeve and mandrel dimensional tolerances compound to prevent obtaining a consistent strain around the hole. On the other hand, with sleeveless expansion of holes in, e.g., titanium, mandrel forces tend to be relatively large, and accordingly, a significant amount of galling and material pick up can occur on the mandrel as it traverses the hole, which precludes both the use of a pull-type solid mandrel or a split mandrel, and a re-use of either. Accordingly, this invention incorporates a sleeveless, "push-only" process, in which the expansion mandrel is used only once, to better control forces and strains and minimize the chances of the mandrel being jammed in the hole or scoring it, and varying the hole size prior to expansion as required to attain the desired target strain. Mandrel costs can be controlled by specifying only one, or at most, two standard mandrel sizes (e.g., one basic size and one larger size for re-test or rework) and adjusting the hole size prior to expansion as required to attain the desired target strain.

As illustrated in FIG. 2, the first step of the exemplary method comprises drilling and reaming a test through-hole 26 at the desired location in the manufactured part 28 to a standard hole size, e.g., 0.3750, +0.0000/−0.0020 inch. The hole is preferably located in an area of the part that will not be highly loaded in service, and away from other stress concentrations. After the hole has been drilled and reamed, the hole is deburred at a first, or front, mandrel entry end 30, and the hole is lubricated internally, e.g., with molybdenum disulfide grease.

The mandrel 10 is preferably made of a strong, hard material, such as a structural ceramic (e.g., silicon nitride) or a suitable tool steel with a hard, low-friction coating. With reference to FIG. 1, the diameter B of the first end portion 16 of the mandrel is designed to serve as a pilot, and is therefore made slightly smaller than the test hole 26 initial diameter H. The diameter of the second, hole-expanding portion 18 of the mandrel is related to the initial test hole diameter H by the relationship, $$D = \left(\frac{e}{100} + 1\right) \cdot H,$$

where e is the minimum percent elongation, or acceptable target strain, in the specification of the part 28 (e.g., 6.0 percent for certain titanium alloy castings), and H is the diameter of the test hole.

The mandrel 10 is then lubricated, and the pilot end portion 16 is inserted in the first, entry end 30 of the test hole 26, as illustrated in FIG. 2. Alternatively, the mandrel may be furnished with a baked-on, or otherwise applied, thin-film lubricant to avoid the need for lubricating it prior to the test. A reusable stop 32 made from a high-strength material may be used to control the amount of mandrel travel, but is not required if the process is performed slowly and can be easily halted as the mandrel reaches its maximum amount of engagement near the entry end 30 of the test hole, i.e., when the second end 14 of the mandrel is about flush, or coplanar with, the entry end of the test hole. It may be noted that the mandrel may advantageously incorporate a bearing surface comprising a spherical segment at the second end thereof to define a point contact with the stop 32, to compensate for any misalignment of the mandrel with the test hole, as well as to facilitate expanding test holes that are not precisely normal to the mandrel entry end of the hole.

As illustrated in FIG. 2, an annular support element 34 having an internal diameter larger than H may be disposed against a back surface of the part 28 and aligned coaxially with the test hole 26 to react against the pushing force of the mandrel 10 and thereby minimize any deflections in the part when the mandrel is pressed into the test hole. The support element may comprise either a suitably strong hollow cylinder, as illustrated in FIG. 2, or simply a thick plate with a hole that is larger than and disposed concentrically with the test hole. Of importance, it should be noted that the thickness of the part should be equal to or greater than the test hole diameter H, to minimize permanent axial deformation of the part near the test hole.

Figure 3:
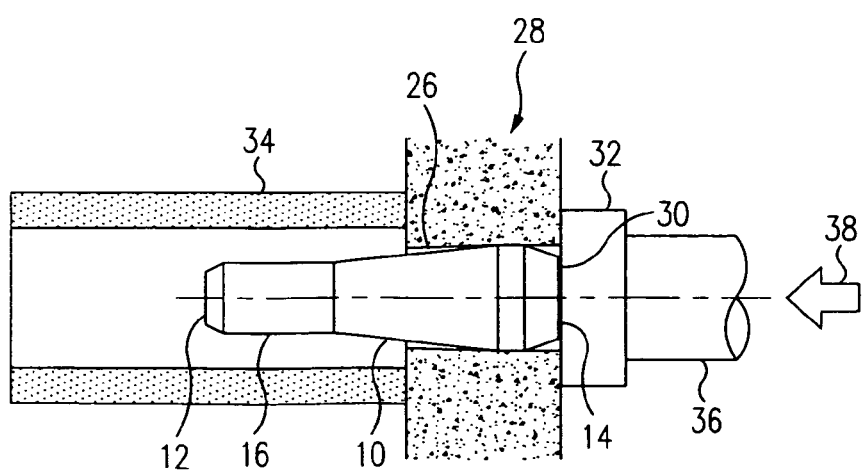
FIG. 3 is a partial cross-sectional elevation view of the mandrel after being pressed into the test hole of the part.
Figure 4:
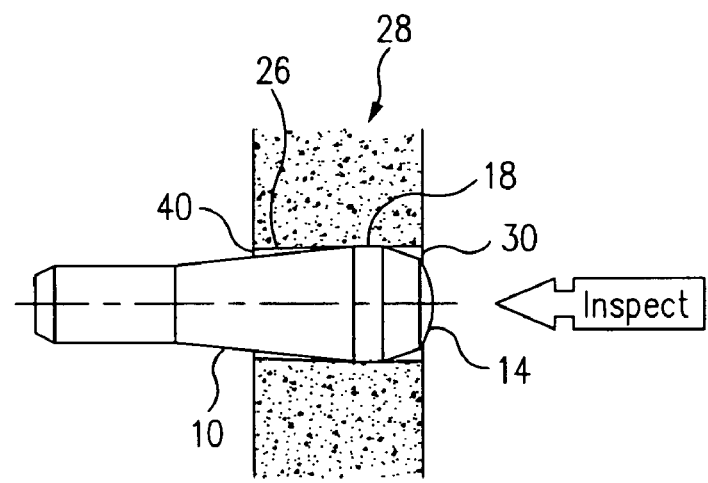
FIG. 4 is a partial cross-sectional elevation view of a region of the part adjacent to the first end of the hole being inspected for radial cracks.

The mandrel 10 and the optional stop 32 are pushed slowly toward the part 28 by a benchtop press ram 36 in the direction of the broad arrow 38 in FIG. 2, until the stop is disposed against the surface of the part and the second end 14 of the mandrel is about coplanar with the first end 30 of the test hole 26, as illustrated in FIG. 3, which corresponds approximately to the point of maximum mandrel engagement of the hole near the mandrel entry end 30 thereof. At this point, the ram and stop are pulled away from the mandrel, and the surface of the part adjacent to the first end of the expanded hole is inspected for radial cracks caused by the tensile expansion, or elongation, of the hole, as illustrated in FIG. 4. The inspection may be performed visually, using conventional light and optical magnifiers, or, e.g., by use of a fluorescent dye penetrant. It may be noted that, by performing the inspection at the maximum expansion of the hole, any radial cracks present will be open and notorious, and therefore more easily detected. As the circumferential strain at the edge of the enlarged test hole has been set by design to match the minimum elongation requirement e in the specification of the part, the presence of detectable radial cracks indicates that the casting does not meet the specification, i.e., the part failed the test, and the absence of such cracks indicates that it passed.

If no radial cracks are found in the part 28 adjacent to the first end 30 of the test hole 26, the test is continued at the back side of the part, and the procedure followed with respect thereto depends on the local thickness of the part. For test holes that are relatively shallow, i.e., those in which the second, expanding portion 18 of the mandrel 10 is disposed adjacent to a second, or mandrel exit end 40 of the test hole after the mandrel is initially pressed in, both the front and back surface inspections may be conducted concurrently, by simply turning the part over and inspecting the part adjacent to the second end of the expanded test hole for radial cracks.

However, for relatively deep test holes 26, i.e., those in which the second, expanding portion 18 of the mandrel 10 is spaced apart from the second end 40 of the test hole after the mandrel is initially pressed in, as illustrated in FIG. 4, it is desirable to press the mandrel further into the hole, until the second portion of the mandrel is disposed at about the second end of the test hole, so that the hole is fully expanded throughout it entire length, before performing an inspection for radial cracks at the second end thereof.

Figure 5:
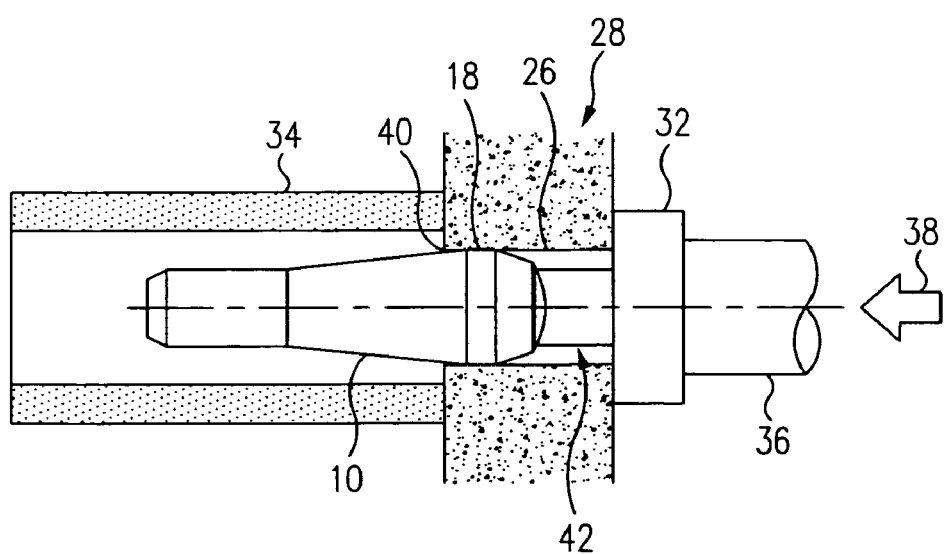
FIG. 5 is a partial cross-sectional elevation view of the mandrel being pressed further into the test hole of the part.
Figure 6:
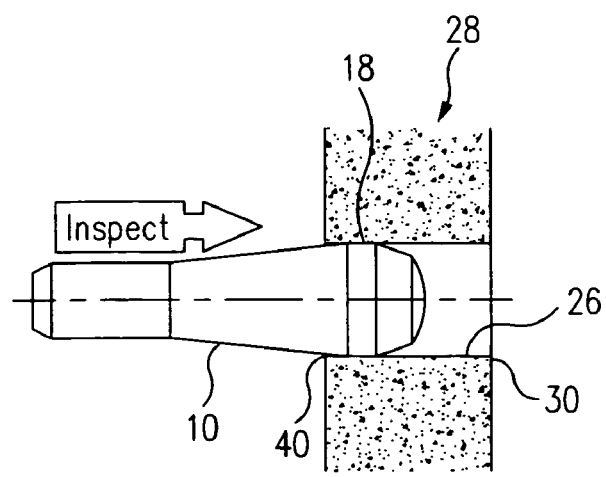
FIG. 6 is a partial cross-sectional elevation view of a region of the part adjacent to a second end of the test hole being inspected for radial cracks; and, FIG. 7 is a partial cross-sectional elevation view of the mandrel being pressed out of the part.

As illustrated in FIG. 5, this may be effected using a short insert 42 disposed on the optional stop 32. The length of the insert 42 is selected such that the second portion 18 of the mandrel 10 is disposed adjacent to the second, or mandrel exit end 40 of the test hole 26, as illustrated in FIGS. 5 and 6, and the diameter of the insert is, of course, selected to be less than the diameter H of the test hole, so that the insert fits in the hole without interference. As illustrated in FIG. 6, after the test hole has been fully expanded by this second pressing of the mandrel, the back side of the part 28 may be inspected adjacent to the second end 40 of the test hole for radial cracks in a manner similar to that conducted on the front side.

Figure 7:
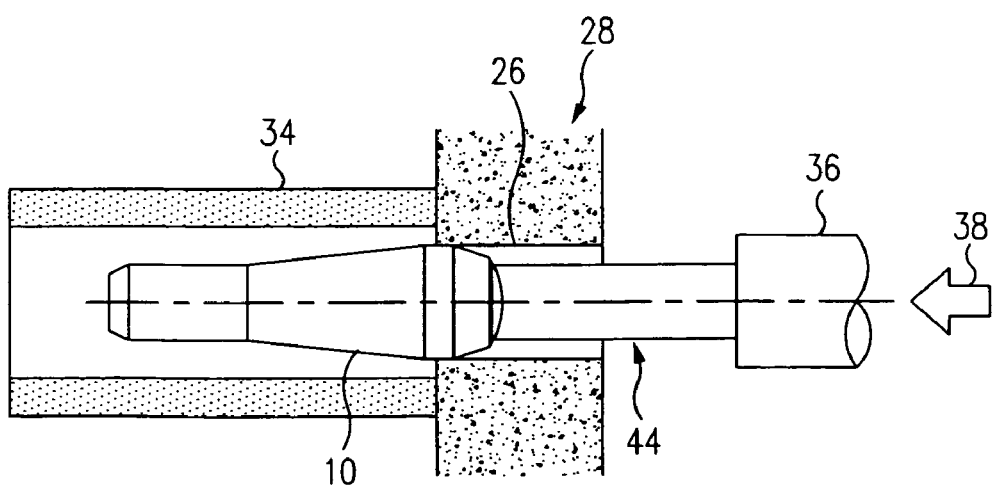

The test process is completed by expelling the mandrel 10 completely from the test hole 26, as illustrated in FIG. 7. This may be effected by pressing against the second end 14 of the mandrel with the press ram 36 and a second insert 44 of an appropriate length. Preferably, the mandrel is then discarded, as it may have been rendered unsuitable for re-use, either by damage or by the accretion of a coating of material from the inspected part 28 as a result of its having been pressed through the test hole. After the mandrel has been ejected from the part, the test hole may be cleaned and inspected for signs of scoring or gouges, and can either be further processed (e.g., reamed) and filled with a fastener, or simply left as an open hole. The part may then be tagged for appropriate subsequent disposition, i.e., rejection, reworking, or further processing. It should be noted that, since the method and apparatus of the invention functions to cold-work the test hole, the possible detrimental effect of the test hole on fatigue performance of the tested part is substantially mitigated.

By now, those of skill in this art will appreciate that many modifications, substitutions and variations can be made in and to the materials, apparatus, configurations and methods of implementation of the present invention without departing from its spirit and scope. Accordingly, the scope of the present invention should not be limited to the particular embodiments illustrated and described herein, as they are merely exemplary in nature, but rather, should be fully commensurate with that of the claims appended hereafter and their functional equivalents.

What is claimed is:

1. An apparatus for a nondestructive, in-situ verification of a minimum tensile elongation specification e of a manufactured part, where e is expressed as a percent elongation, the apparatus comprising:
an elongated mandrel having:
opposite first and second ends;
a solid, cylindrical first portion disposed adjacent to the first end and having a constant diameter B;
a solid, cylindrical second portion disposed adjacent to the second end and having a constant diameter D; and,
a first axial taper extending between the first and second portions.

2. The apparatus of claim 1, wherein the mandrel further comprises:
a second axial taper extending between the first end and the first portion; and,
a third axial taper extending between the second portion and the second end.

3. The apparatus of claim 1, wherein:
the part includes a cylindrical test hole formed thorough it, the test hole having opposite first and second ends and a diameter H;
B is smaller than H; and, $$D=[(e/100)+1]\cdot H.$$

4. The apparatus of claim 1, wherein the second end of the mandrel is rounded.

5. The apparatus of claim 1, wherein an exterior surface of the mandrel is coated with a hard, low-friction coating.

6. The apparatus of claim 1, wherein the mandrel is made of a structural ceramic or a tool steel.

7. The apparatus of claim 1, wherein the mandrel is made of silicon nitride.

8. The apparatus of claim 1, wherein an exterior surface of the mandrel is coated with a thin-film lubricant.

9. The apparatus of claim 3, further comprising an annular support element having an internal diameter larger than H disposed against a back surface of the part and aligned coaxially with the test hole.

10. A method for a nondestructive, in-situ verification of a minimum tensile elongation specification e of a manufactured part, the method comprising:
forming a cylindrical test hole through the part;
providing an elongated cylindrical mandrel having a pilot portion and a hole expanding portion, wherein the hole expanding portion is sized to effect a circumferential strain of e at the edge of the test hole when inserted therein;
inserting the pilot portion of the mandrel into a first end of the test hole in the part;
pressing the mandrel fully into the hole; and,
inspecting the part adjacent to at least one of the first end and an opposite second end of the test hole for radial cracks.

11. The method of claim 10, further comprising:
pressing the mandrel further into the hole, until the hole expanding portion of the mandrel is disposed at the second end of the test hole; and,
inspecting the part adjacent to at least one of the first and second ends of the test hole for radial cracks.

12. The method of claim 10, further comprising lubricating an exterior surface of the mandrel before inserting the first end thereof into the test hole.

13. The method of claim 10, wherein the part comprises a casting, a forging, a molded part or a premium mill product.

14. The method of claim 10, wherein the part comprises aluminum, titanium, magnesium, copper, bronze, beryllium, steel, a nickel alloy, a heat-resistant alloy or a refractory alloy.

15. A method for a nondestructive, in-situ verification of a minimum tensile elongation specification e of a manufactured part, where e is expressed as a percent elongation, the method comprising:
forming a cylindrical test hole thorough the part, the test hole having opposite first and second ends and a diameter H;
providing an elongated mandrel having:
opposite first and second ends;
a first cylindrical portion disposed adjacent to the first end and having a diameter B, where B is smaller than H;
a second cylindrical portion disposed adjacent to the second end and having a diameter D, where $D=[(e/100)+1] \cdot H$; and,
a first axial taper extending between the first and second portions;
inserting the first end of the mandrel into the first end of the test hole;
pressing the mandrel into the test hole, until the second end of the mandrel is about coplanar with the first end of the hole; and,
inspecting the part adjacent to at least one of the first and second ends of the test hole for radial cracks.

16. The method of claim 15, further comprising:
pressing the mandrel further into the test hole, until the second portion of the mandrel is disposed at about the second end of the hole; and,
inspecting the part adjacent to at least one of the first and second ends of the test hole for radial cracks.

17. The method of claim 15, further comprising lubricating an exterior surface of the mandrel before inserting the first end thereof into the test hole.

18. The method of claim 15, further comprising disposing an annular support element having an internal diameter larger than H against a back surface of the part and coaxially aligned with the test hole.

19. The method of claim 15, wherein the part comprises a casting, a forging, a molded part or a premium mill product.

20. The method of claim 15, wherein the part comprises aluminum, titanium, magnesium, copper, bronze, beryllium, steel, a nickel alloy, a heat resistant alloy or a refractory alloy.

* * * * *